United States Patent [19]

Spinello

[11] Patent Number: 4,531,914

[45] Date of Patent: Jul. 30, 1985

[54] DENTAL DEVICE AND METHOD FOR GINGIVAL RETRACTION AND CONDITIONING

[76] Inventor: Ronald P. Spinello, 523 Post Ave., Westbury, N.Y. 11590

[21] Appl. No.: 524,336

[22] Filed: Aug. 18, 1983

Related U.S. Application Data

[63] Continuation-in-part of Ser. No. 287,375, Jul. 27, 1981, abandoned.

[51] Int. Cl.³ ............................................. A61C 5/14
[52] U.S. Cl. ..................................... 433/136; 433/48; 433/80; 433/215; 604/375; 604/373; 424/28
[58] Field of Search ................. 433/136, 215, 48, 40; 128/296, 261, 268, 127, 131; 424/28; 106/35; 604/358, 365, 11

[56] References Cited

U.S. PATENT DOCUMENTS

| | | | |
|---|---|---|---|
| 335,799 | 2/1886 | Darby | 433/215 |
| 688,446 | 12/1901 | Stenpel, Jr. | 128/268 |
| 974,295 | 11/1910 | Pond | 128/268 |
| 1,550,425 | 8/1925 | Burlew | 433/136 |
| 2,152,391 | 3/1939 | Spahn | 433/136 |
| 3,238,620 | 3/1966 | Robertson | 433/215 |
| 3,386,440 | 6/1968 | Cohen | 128/268 |
| 3,416,527 | 12/1968 | Hoef | 128/260 |
| 3,602,993 | 9/1971 | Kenney | 433/40 |
| 3,625,215 | 12/1971 | Quisling | 128/260 |
| 3,925,895 | 12/1975 | Kliment et al. | 433/224 |

*Primary Examiner*—John J. Wilson
*Attorney, Agent, or Firm*—Eisenman, Allsopp & Strack

[57] ABSTRACT

A dental method and apparatus for swiftly performing gingival retraction and conditioning in which a mass of moldable coherent plastic, preferably thixotropic, is lightly pressure molded both into and around the gingival trough of a prepared tooth to apply substantially balanced forces around the gingival flap which maintain the gingival trough without distortion. The moldable mass is rendered hydrosorbent at least on its surface by intimately bonded absorbent fiber, enabling it to absorb all the liquids and debris which would normally preclude the material from flowing into the trough. To effect a slight enlargement of the trough and to prevent prolapse in the case of very narrow troughs a preliminary bead of flowable thixotropic material can be injected into the trough to transmit light lateral outward pressure on the flap when pressed into the trough by the moldable absorbent mass.

27 Claims, 12 Drawing Figures

DENTAL DEVICE AND METHOD FOR GINGIVAL RETRACTION AND CONDITIONING

RELATED APPLICATIONS

This application is a continuation-in-part of my co-pending application Ser. No. 287,375, filed July 27, 1981, and now abandoned.

BACKGROUND OF THE INVENTION

This invention relates to dentistry and in particular to devices and methods for gingival retraction and localized conditioning as a step in complex dental procedures including tooth reconstruction and treatment.

Gingival retraction and conditioning is a time-consuming and somewhat traumatic procedure. It is required for example, in the process of fabricating tooth crowns which must seat well into the sub-gingival areas around the tooth, not to exceed the depth of the sulcus. To cast the crown, a precision mold must be taken of the tapered prepared tooth to the extremes of the prepared gingival trough, which is the tiny open groove between the gingival tissue and the ground-down neck or prepared portion of the tooth, so that the fabricated crown will extend into the sub-gingival area and also mate perfectly with all opposing tooth surfaces. To make an accurate mold, the gingival trough must be kept open and freed of blood, saliva and debris in a process known as gingival retraction.

An early and largely superseded technique of gingival retraction involves the use of a malleable copper sleeve filled with impression material and adapted to be carefully pressed and manipulated over a tooth to stress and distend the gingiva and squeeze out the blood and saliva from the trough, after which the impression is taken. It is an accurate but painstaking procedure, difficult to do well, often wasteful of time and traumatizing to the gingival tissue.

The state of the art technique for gingival retraction superseding copper sleeves, involves looping an absorbent cord preferably treated with a vasoconstricting chemical such as aluminum chloride about the freshly prepared tooth and packing it into the gingival trough using a pointed instrument. Packing the cord into the trough is tedious and wasteful of time (as much as five minutes) because of poor visibility in an extremely confined area coupled with the inherent sponginess of gingival tissue which resists the cord placement. The cord remains in place for several minutes holding the trough open, absorbing saliva and blood in the trough, and treating the traumatized tissue to control further bleeding. It is withdrawn an instant before the critical impression is taken. In addition to the time taken by the dentist installing the cord and the inherent traumatizing of the tissue, the cord has limited absorption ability and does not effectively protect the general area from the influx of additional saliva.

Further, the stressful action of packing the cord can create an artificially enlarged gingival trough extending beyond the sub-gingival line where tooth preparation ends, even to the point of occasionally tearing gingival tissue from the tooth root beyond the sulcus. The subsequent impression not infrequently yields a crown casting having a skirt which extends beyond the prepared portion of the tooth into an area in which the tooth may widen in an almost imperceptible bulge or bump and thereafter narrow into an undercut. The inherent resilience of the polymerized or hardened impression material enables it to be pulled from the undercut over the enlargement, but the memory of its existence endures. As a result, the finished crown, having a rigid elongated skirt smaller at its leading edge than the widest diameter of the tooth parts it is intended to surround, can bind in a slightly elevated position requiring the dentist to perform tedious grinding operations in an attempt to achieve good crown seating and tooth occulusion. This highly undesirable and time-wasting characteristic has become increasingly evident as less malleable and harder casting metals are substituted for costly softer metals such as gold.

Accordingly, it is an object of the present invention to provide a dental device and method for gingival retraction and conditioning which are able without trauma and in a fraction of the time presently required to carry an absorbent medium into the tiny gingival trough around the necks of prepared teeth to absorb all saliva and blood, to entrain particulate debris, to treat against further bleeding and to shield the entire area from encroaching saliva.

A further object of the invention is to provide a dental device and method for gingival retraction and conditioning which do not enlarge the gingival trough beyond its natural elastic limits and thus beyond the line of tooth preparation and which, therefore, result in impressions which yield castings that do not bind before seating fully on the prepared tooth.

SUMMARY OF THE INVENTION

In the method aspect of the invention, gingival retraction and treatment are effected by preparing a tooth for crowning by grinding the side walls into truncated conical configuration with the base disposed in the sub-gingival area not in excess of the depth of the sulcus to define a gingival trough between the ground-down walls of the tooth and the flap of surrounding gingival tissue, and placing on the tooth a body of coherent highly moldable flowable material having hydrosorbent characteristics at least at its surface. Pressure is applied on the body axially with respect to the tooth to cause the material to flow down the conical sides of the tooth both into and outside of the gingival trough, to envelop the gingival flap while absorbing liquid blood and saliva within the trough, thereby allowing the flowable material to substantially fill the trough to establish balanced lateral forces across the flap. It is therefore held gently in its natural position while it is conditioned against further bleeding, with the molded material shielding the entire area from the influx of additional saliva. If it is desired to slightly enlarge the trough without damage to the tissue a two-step process can be employed in which a bead of flowable thixotropic material is first injected into trough followed by the body of flowable hydrosorbent material. The bead then exerts gentle outward pressure on the flap of gingival tissue before the body molds itself over the outer wall of the flap.

Devices and materials for clearing the trough and treating the gingival tissue can take the form of a small body of highly moldable flowable coherent plastic material treated or fabricated to render it hydrosorbent, at least on its surface, but without impairing flowability under light pressure. The body has a volume capable of inundating the treatment site and is molded by light pressure directed along the axis of the tooth, causing it to flow down the sides of the tooth and both into and outside of the gingival trough to absorb blood and saliva and to apply balanced light lateral forces across the gingival flap to hold it in its natural position, or if a preliminary bead has been injected into the trough, to gently push the flap outward to slightly enlarge the trough before the lateral balancing forces come into play. The body of material can be seated in a thin walled open shell sized to match the size of the treatment site and shaped to control the flow along the sides of the tooth into and outside of the trough.

In one preferred embodiment of the invention, the moldable body can be formed of plastic thixotropic medium such as hydrolyzed high polymer silicone which can be rendered hydrosorbent by incorporating fibers. In this embodiment, the balance and placement of fibers and plastic becomes critical because the essential physical property of each medium is antithetical to the other and an imbalance can render the device ineffective. Excess fibers can so effect the moldability of the plastic that it will not enter the gingival trough and excess plastic can render the complex of fibers carried into the trough non-absorbent.

A mass of the thixotropic material sufficient to surround a tooth and its associated gingival area is prepared with a surface which includes an extremely thin layer of non-woven united fibers rendering the surface hydrosorbent. This structure can have a relatively short life before the thixotropic plastic so inundates the fibers that they cannot effectively absorb, but the freshly fiberfaced plastic when pressed onto a prepared tooth will be able to carry certain amounts of absorbing fibers into such small areas as the gingival trough in a matter of seconds. The ability of the mass to convey surface fibers into small or deep crevices can be enhanced by incorporating additional fibers within the body of the mass either randomly or in layers, provided, however, that the amount by weight of the internal fibers be kept in a low ratio to the weight of the plastic.

The life and effectiveness of the product can be further enhanced by incorporating a second thin layer of non-woven fibers in the surface over the first layer without degradation of the flowability of the material. The first layer is gripped by the plastic flowing into interstices in the fiber mass, and the second layer can be joined to the first by means of a thin spray of adhesive or alternatively, the first layer can be formed with enlarged interstices in the form of pin holes or short slits, preferably amounting in the aggregate to a small percentage of the surface area, through which the plastic can flow to establish a mechanical bond with the filaments of the top layer. The resulting structure is capable of flowing into minute crevices such as the gingival trough and of absorbing all liquids in the trough.

The product can be packaged as individual units in a semi-cylindrical carrier shell exposing the absorbent surface and by means of which the device can be pressed onto a prepared tooth either by the dentist or by the patient biting against the shell. Alternatively, the mass with one or two absorbing surfaces can be contained in a lateral sheath in a variety of configurations; rectangular, round, oval or arcuate, for constraining the mass against lateral flow when pressed onto a tooth. When the patient bites on the device, the tooth opposing the prepared tooth will act as a piston, driving the working surface of the material into place around the tooth under the constraint of the lateral sheath. The sheath should be collapsible at least where it encounters other teeth and can be made at least in part of highly absorbent material. Also, the non-working surface can be packed with highly absorbent material such as cotton.

The absorbent layer of fibers is preferably impregnated with a vasoconstricting chemical such as epinephrine or aluminum chloride to arrest bleeding of traumatized gingival tissue. In the case of the two-stage process in which a bead of flowable thixotropic material is first injected into the trough, it is desirable to include the vasoconstrictor in the bead material.

DESCRIPTION OF THE PREFERRED EMBODIMENT

Figure 2:
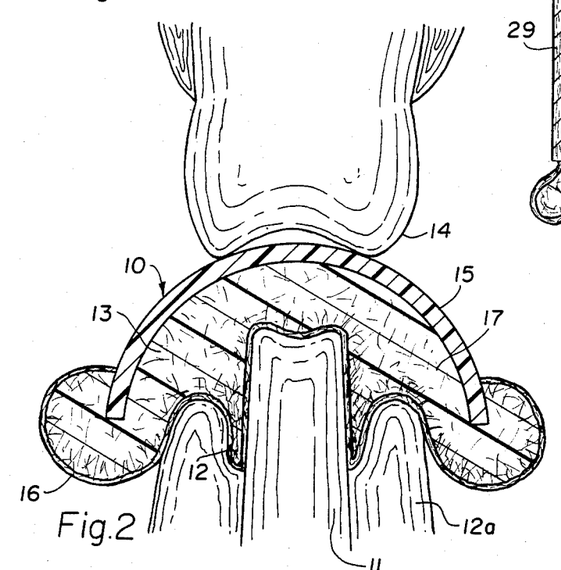
FIG. 2 is a view in enlarged scale taken in cross-section through a prepared tooth and the surrounding gums and showing the absorbent device of FIG. 1 in place on the tooth and retracting the gingival trough.

Referring to FIG. 2, the new method of gingival retraction and conditioning is illustrated in process. The tooth 11 has been prepared for receiving the crown by grinding the side walls down to form a generally truncated conical configuration having its base in the sub-gingival area preferably about two-thirds of the depth of the sulcus, which is the depth beyond which the gingival tissue is tightly bonded to the tooth and which should in no event be disturbed. The process of cutting down the tooth creates the gingival trough 12 which is the space between the surrounding gingival flap formed by tissue 12a. The trough is typically on the order of 1.0 millimeter wide at the top and 3.0 millimeters deep and will be filled with blood, saliva and debris which must be removed and the flow of blood staunched before the highly critical impression for making the crown can be taken.

In accordance with one embodiment of the invention, the gingival trough 12 is cleaned and the tissue conditioned in a swift process which does not distort or distend the gingiva nor, therefore, does it enlarge the gingival trough. While the procedure is characterized in this embodiment in the historical nomenclature "gingival retraction" it will be understood that the gingiva is not driven back from the tooth but is, rather, carefully and gently sustained in its natural position around the prepared tooth. To this end, a body 10 of highly moldable material 13 having hydrosorbent characteristics at least at its surface 16, is molded or flowed by means of light pressure applied generally axially of the tooth, causing it to flow down the side of the prepared tooth and both into and outside of the gingival trough to envelop the gingival flap in a matter of seconds while absorbing the liquid in the trough. The forces across the flap remain balanced to hold it precisely in its natural position. The addition of a vasoconstrictor such as aluminum chloride stops the flow of blood where tissue might have been damaged in the prior grinding operation. The coherent mass 17 is withdrawn an instant before the impression is taken. Thus, the invention provided non-traumatic and swift gingival retraction and conditioning in which the moldable material is flowed on both sides of the gingival flap either under the light pressure of the tooth 14 above pressing on a thin walled semi-cylindrical container or shell 15 or, if preferred, by finger pressure by the dentist.

The core material 13 is formed of a coherent highly moldable plastic material of high viscosity. A highly moldable material which is nevertheless sufficiently coherent to be handled as a mass can be defined as thixotropic or dilatant. An example of such material is hydrolyzed high polymer silicone commonly known as silicone putty. Inorganic fillers, such as boric acid, can be used in the material to control its viscosity or rate characteristics without impairing its ultimate flowability. Other examples of materials having thixotropic properties include hydrocolloids and certain unpolymerized synthetic rubbers (butanes), certain gels and solgels. The thixotropic materials are non-absorbent and impervious to moisture and cannot, therefore, be flowed into a gingival trough filled with blood and saliva which block its entry even though it will readily flow into a dry trough. In accordance with the invention, the thixotropic core 13 can be rendered hydrosorbent by having intimately bonded thereto a thin outer layer 16 of non-woven absorbent fibers, such as wood fibers used in making absorbent papers, cotton fibers or the like. The non-woven fiber layer is formed as an extremely thin paper-like sheet of united fibers preferably rolled to a thickness of approximately 0.03 to 0.07 millimeter. The interstices in the fiber sheet placed against the surface of the thixotropic core will receive projections of the thixotropic material in the form of a myriad of tiny fingers which mechanically bond the fiber layer intimately to the core. The product so formed, particularly if freshly prepared, when pressed over a tooth will retain its ability to flow into tiny depressions such as the gingival area, but it will also carry fibers into the trough where they absorb the liquids and allow full penetration of the core material. There is a tendency, particularly if the trough is deep and narrow, for the fiber sheet to be torn away by the distending plastic core to expose a leading edge of the base core material which is non-absorbent. To overcome this undesirable characteristic in accordance with the present invention, fibers 17 (best seen in FIGS. 8 and 9) are entrained and dispersed in the body of the thixotropic mass, particularly in the space immediately beneath the absorbent surface 16. The proportion of embedded fibers must be closely controlled. If embedded in excess quantity, the material loses its essential moldable and flowable characteristics. Using high polymer silicone putty as the base, and fibers from paper as the entrained material, a ratio by weight of 3 percent fiber fill has been found to be effective, although the quantity can range between 2 and 4 percent. It should be noted that the fiber-impregnated thixotropic mass is not absorbent per se but the entrained fibers apparently react mechanically with the surface fibers to prevent tearing and parting of the absorbent sheet over highly distended portions of the core material, such as those penetrating the gingival trough.

The single surface layer of absorbent material as described above can, under certain circumstances, exhibit a characteristic of diminishing effectiveness. If the thixotropic core, with the passage of time or due to pressure on the surface, penetrates the absorbent layer too deeply in establishing the mechanical bond or, if the volume of core material in the layer becomes excessive, the ability to asborb liquids declines. This effect can be prevented in accordance with the invention by the structure shown in FIGS. 8 and 9.

Figure 8:
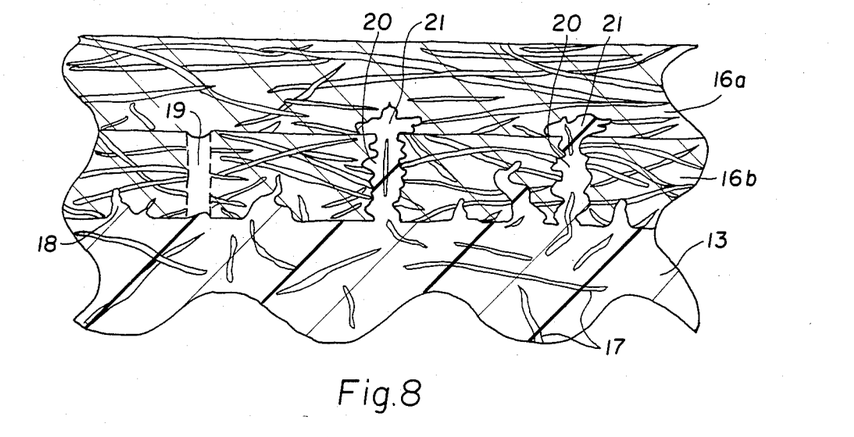
FIG. 8 is a diagrammatic view, highly enlarged and not in scale, illustrating the surface and sub-surface characteristics of one form of the invention.

Referring to FIG. 8 in which a very small portion of the device is shown in highly enlarged scale, the thixotropic body material 13, in addition to entraining randomly spaced fibers 17 in an amount corresponding to approximately 3 percent by weight and distributed more or less uniformly throughout, has attached to its upper surface two discrete layers 16a and 16b of nonwoven fibers. Each layer is preferably approximately 0.03 to 0.07 millimeter in thickness. The lower layer is intimately bonded to the core by a myriad of fingers 18 penetrating interstices among the fibers. The lower layer is also formed with an array of perforations 19 amounting in the aggregate to less than 10 percent of its area and through which the thixotropic material penetrates to engage the underside of the upper layer 16b and mechanically bond with its fibers. As seen in the drawing, the left-hand aperture 19 is shown empty of the flowable material. In the other apertures, the core material 20 has spread among the fibers closest to the aperture and into the fibers of the upper layer in a head 21 among the fibers, thereby forming a mechanical bond holding the layers in place. The illustration of FIG. 8 is diagrammatic to show the principles of the invention and is not intended to be in scale. For example, the apertures 19 are preferably made substantially larger in diameter than the thickness of the layers in order to hasten the bonding of the upper layer. However, by severely limiting the direct exposure of the upper layer to the thixotropic core, saturation of the upper layer or significant encroachment at its surface by the core material is prevented and the ability of the fibers to absorb liquid is preserved. The double layer construction of FIG. 8 has a long shelf life and can withstand substantial molding and working without bringing deleterious quantities of the thixotropic base material to the surface.

Figure 9:
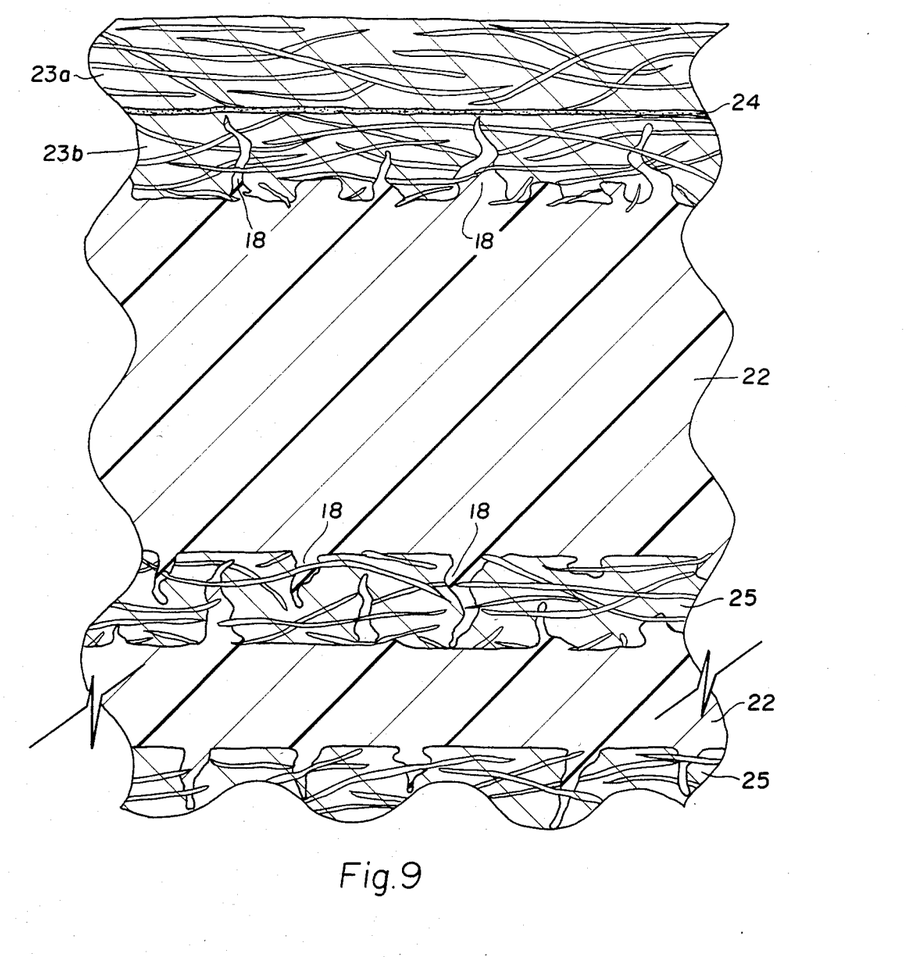
FIG. 9 is a view similar to that of FIG. 8, illustrating another form of the invention.

In the arrangement of FIG. 9, there are shown thixotropic core layers 22 which do not have fibers uniformly dispersed throughout their mass as in the case of FIG. 8. Instead, one or more concentrated fiber layers 25 are embedded in parallel spaced-apart fashion, but nevertheless in substantially the same overall weight ratio as in the case of the more thinly distributed fibers of FIG. 8. The thickness of the core material layer 22 which is free of fibers is extremely small, on the order of 0.5 millimeter, so that when the device is molded onto a tooth and the core material distends into a tiny projection entering the gingival trough, the interior layer of fibers can migrate to the upper layer where they strengthen the upper layer against tearing. In FIG. 9, the surface layers 23a and 23b are bonded by an adhesive layer 24 in the form of an aerosol spray of contact cement kept thin enough so as not to impair the porosity of the laminated structure, although it will be understood that mechanical bonding by fingers of core material, as in FIG. 8, can be used as can a combination of both techniques. It will be understood also that the internal fiber layers 25, while shown parallel to the surface layers 23a and 23b, may be at angles, including perpendicular, thereto.

In each of the embodiments of FIGS. 8 and 9, the non-woven fiber surface is sufficiently pliant to permit the thixotropic core material to flow into small crevices, such as the gingival trough, carrying with it a layered mass of absorbent fibers which absorb substantial volumes of ambient liquids, thus clearing the trough. A 0.1 millimeter dual layer of fiber, for example, has the ability to absorb all of the liquid contained in a trough 3 millimeters deep without impeding the ability of the thixotropic material to flow into the space. Unexpectedly, the balance of forces inherent in the axially directed molding action around the tooth and the gingival tissue coupled with the unique physical characteristics of the thixotropic material effect a complete gingival retraction in a matter of seconds gently and without trauma. The fibers, particularly the surface layers, impart sufficient integrity to the device to enable it, notwithstanding the thixotropic mass, to be easily handled and to maintain its initial geometry until deliberately molded over a tooth.

Figure 1:
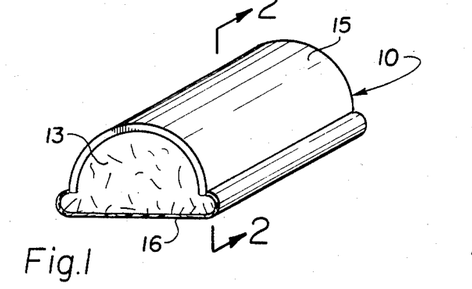
FIG. 1 is a view in perspective of one embodiment of the invention.
Figure 3:
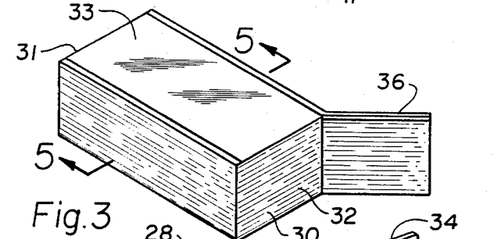
FIG. 3 is a view in perspective showing another embodiment of the invention.
Figure 4:
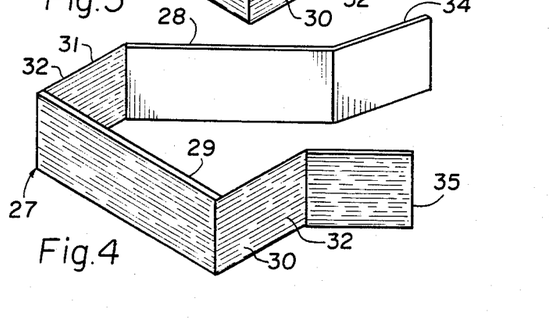
FIG. 4 is a view in perspective showing the lateral container of the unit of FIG. 3 separated from moldable body portion.
Figure 5:
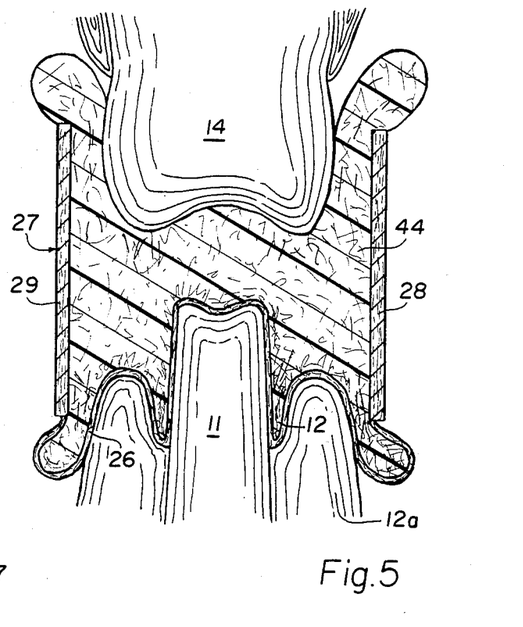
FIG. 5 is a view in cross-section through a tooth prepared for crowning, showing the embodiment of FIG. 3 in place in the patient's mouth and actuated by the opposing upper tooth.

Referring to FIGS. 3 to 5, there is illustrated another embodiment of the invention in which the upper tooth 14 rather than bearing down on the shell or housing portion 15 as shown in the device 10 of FIGS. 1 and 2, bears down on the top of a column 44 of thixotropic material to press the column and its bottom surface 26 against the prepared tooth 11 to urge it to flow into the gingival trough 12. In this modification, at least the lower surface 26 includes an absorbent layer of fibers of any one of the types described above. The body or mass 44 of thixotropic material is contained in a lateral housing or container, best illustrated in FIG. 4. The housing 27 is comprised of a pair of side walls 28 and 29, preferably formed of an absorbent material, such as semi-rigid cardboard. The cardboard sides 28 and 29 are attached to a continuous flexible strip 30 having high tensile strength, such as Mylar film or filament-reinforced plastic tape. The flexible strip bridges the side portions at its front and back 31 and 32 and is wrapped around a rectangular block 33 of thixotropic core material, at least one of the exposed surfaces of which has an absorbent layer affixed thereto. The free ends of the flexible strip 30 have affixed thereto semi-rigid cardboard tabs 34 and 35 which are brought together and secured to form a handle 36, as shown in FIG. 3. When the device is pressed down over the prepared tooth, either by the dentist pressing with his fingers or by means of the patient's own tooth, the flexible end walls 31 and 32 will be collapsed while still forming a bridge restricting the flow of the thixotropic material out the ends of the device, thereby concentrating the molding forces over the treated area.

Figure 6:
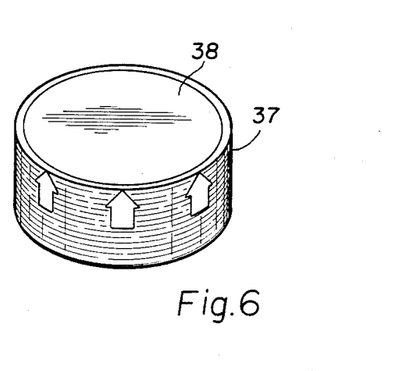
FIG. 6 is a view in perspective of another embodiment of the invention.

Referring to FIG. 6, there is illustrated a simplified version of the device in which the mass of moldable thixotropic material is rounded and enveloped by a lateral wall 37 of flexible sheet material having good tension characteristics similar to the material of the strip 30 in FIG. 4. One or both of the exposed end surfaces of the thixotropic core 38 is covered with an intimately bonded layer of absorbent material. In the illustration of FIG. 6, the single absorbent surface is identified by directional arrows. The device when clenched between the teeth, will conform to the opposing surfaces and at the same time, the flexible wall 37 will collapse where it interferes with other teeth. The arrangement of FIG. 6 is particularly useful for use in a number of different locations in the mouth, as it can be molded by the dentist into various elongated ovals or into an arcuate configuration useful where the tooth line curves.

Figure 7:
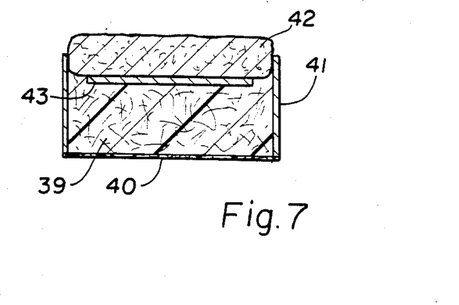
FIG. 7 is a view in cross-section of another embodiment of the invention.

Referring to FIG. 7, there is illustrated a further modification of the design in which the thixotropic core material 39 and the absorbent intimately bonded surface 40 occupy only a portion of the height defined by the side walls 41. A highly absorbent material, such as a cotton wad 42, is fitted in the space on the non-working side of the core 39. If desired, a semi-rigid barrier 43 can be inserted between the absorbent cotton 42 and the thixotropic core 39 to increase the downward pressure on the moldable material. Substantial clearance between the edges of the semi-rigid barrier 43 and the side walls affords pressure relief.

In each of the embodiments of the invention, it is preferred that the absorbent surfaces have impregnated therein a vasoconstricting chemical, such as epinephrine or aluminum chloride, to assist in conditioning the gingival tissue by controlling the blood flow. The chemical in the dry powdered form can also be incorporated in the plastic core or body medium as well as in the filler fibers, preferably by soaking the fibers in a liquid solution of the chemical, drying and thereafter incorporating in the core material.

A characteristic which is common to all of the embodiments of the invention described above is rapid balancing of the forces across the gingival flap imposed by the flowable thixotropic material as it flows down both sides of the flap. This positions the flap in its natural position and otherwise prepares the site for the subsequent step of taking the impression of the tooth walls and the surrounding trough so that a substantially perfectly fitting crown can be cast. In certain situations, however, it may be desired to retract the gingival tissue by forcing it outwardly away from the tooth wall to form an enlarged trough. The only generally known techniques for such gingival retraction involve the use of either copper sleeves or retraction cords which are pressed hard into the trough with substantial attendant trauma.

In accordance with the present invention, however, gingival retraction can be accomplished free of trauma and more swiftly than prior art techniques. Broadly the retraction is accomplished by gentle fluid pressure in which, before the pressure forces across the gingival flap are balanced, differential pressures are established which gently urge the flap outward while clearing the trough of liquids and debris.

Figure 10A:
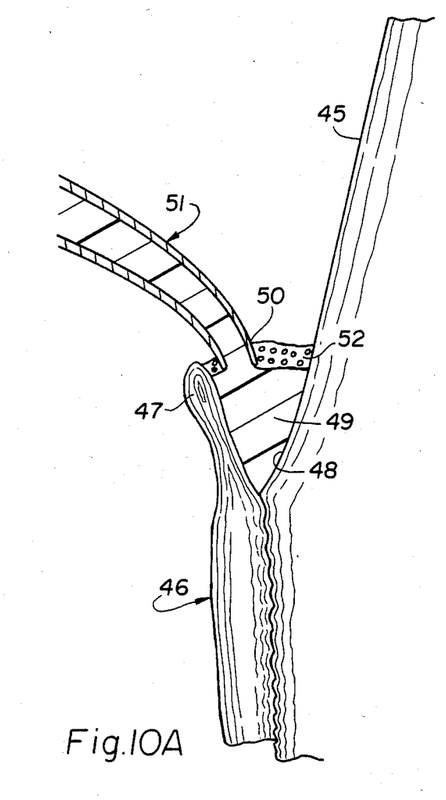
FIGS. 10A, 10B and 10C are a series of corresponding views in cross-section illustrating another embodiment of the invention.
Figure 10B:
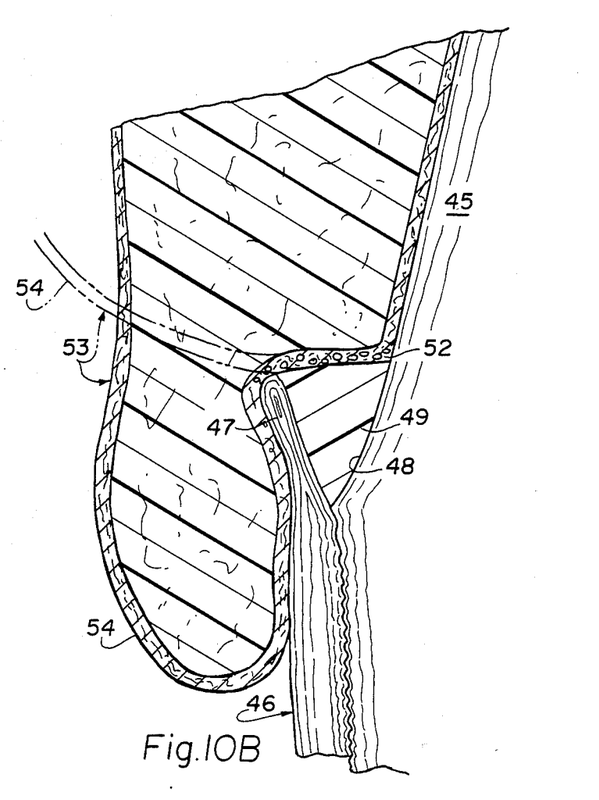
Figure 10C:
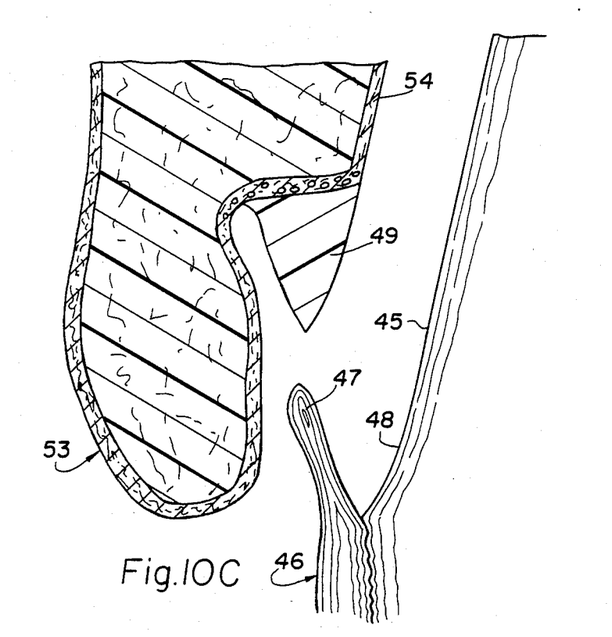

Referring to FIGS. 10A, 10B and 10C there is shown the left side portion of a prepared tooth 45 and surrounding gingival tissue 46 including a gingival flap 47 defining a gingival trough 48. The gingival flap 47 is, similarly to the rendition in FIGS. 2 and 5, somewhat diagramatic rather than being a scaled anatomically precise rendering. It is intended to represent a gingival flap which is narrow and therefore soft, fragile and lacking in resilience. Such tissue is especially difficult to deal with in retraction procedures because it is most apt to be damaged and, more important, to tear away from the root of the tooth, creating overhangs which result in impressions from which mal-fitting crowns are cast. Also, such soft narrow flap tissue is subject to prolapse against the tooth, making an impression of the trough impossible.

Referring to FIG. 10A, the gingival trough 48 is shown having injected into it a bead of flowable thixotropic material 49 extruded from the tip 50 of a dental syringe 51. The flowable material 49 is preferably in the middle range of viscosities and somewhat less viscous than the material of which the moldable bodies 10 and 27 (FIGS. 2 and 5) respectively, are formed but is preferably of the same general character. The viscosity is selected to achieve an extrudable coherent bead which will flow into the trough but not so viscous that it is difficult to make it stay in the trough, particularly at the point of cutting off the flow and withdrawing the syringe. Also, the viscosity of the bead is related to its ability to be united as a single structure with the material of the following mass of treating material, as described below. At the lowest levels of viscosity the bead becomes less capable of joining with the following mass. As the bead flowable material 49 is injected into the gingival trough around the tooth, it displaces the liquids in the trough and entrains particulate matter which might be left over from the grinding operation. The material 49 is preferably treated with a vasoconstricting agent of the type previously described and it may or may not include entrained fibers depending on the degree of viscosity desired. As best seen in FIG. 10B, the bead of material 49 is flowed into the trough in sufficient amounts to substantially fill it. The filling step of the process is essentially gentle and nontraumatic with the pressure of the flowable material within the trough exerting light pressure outwardly on the gingival flap 47 causing the trough 48 to widen slightly. The displaced material 52 from the bottom of the trough appear on the surface of the injected material.

A mass or body 53 of flowable thixotropic fiber-impregnated and coated material 54 corresponding to the material 13 of FIG. 2 (only a portion of which is repeated in FIG. 10B) is pressed down over the prepared tooth and filled trough. The flowing material first engages the material 52 above the head in the trough at which time absorbent layer 54 absorbs the displaced material 52. In addition, a gentle downward pressure on the gingival tissue and the trough can act to further move the gingival flap 47 away from the tooth in a gentle retraction action. The time at which this occurs in the process is shown by the dot-dash outline to the left of the trough in FIG. 10B. As the moldable body 53 is pressed further down over the tooth and gingival tissue, a portion will flow over and around the gingival flap 47 after which the pressure forces across the gingival flap 47 become balanced in a manner similar to the action of the moldable bodies 10 and 27 of FIGS. 2 and 5. Additional vasoconstricting materials can be incorporated in the flowable body 53 particularly on the surface thereof. The materials of the injected bead 49 and the flowable body 53 are compatible and self-adhering, a characteristic which is augmented by the fiber content of the flowable body 53. Thus the bead 49 and the body 53 unite as a single unitary structure.

Referring to FIG. 10C, the combined bead 49 and moldable body 53 are shown being withdrawn from the tooth leaving behind a gently retracted and fully conditioned gingival trough free of liquids and particulate matter and in condition for the immediate taking of the impression from which the crown of the tooth will be fabricated.

The ability of the bead 49 and the moldable body 53 to unite across the absorbent layer 54 is essential to the successful practice of this embodiment of the invention. As stated, the viscosity for the bead as it is flowed into the gingival trough should be sufficiently high to form a coherent packing in the trough. Commercially available silicone base materials used for impression taking can be used including those sold under the trademarks Reprosil, Citricon Base, Cuttersil Putty, and Permagum. The materials are used in the syringe without the associated activators because it is not essential that they polymerize in situ. Such polymerization is not, however, incompatible with the process and could in fact be desirable if the problems of timing and the additional step of mixing can be tolerated. Also, when the two-stage process involving the injected bead followed by the flowable hydrosorbent body is used, it should be noted that the body can be more viscous because it need not penetrate the depths of the trough; essentially it operates to apply gentle pressure to the tissue and the injected bead.

While the invention has been described having reference to the preferred embodiments, it will be understood that it can take other forms and arrangements without departing from the spirit of the invention. For example, the expendible or disposable housings described above can be replaced by re-usable housings or carriers of a variety of shapes and sizes. The device can be formed in the shape of small toroids adapted to be fitted over the prepared neck of the tooth and then molded into the gingival trough. Also, the device can be used for hemostasis to control bleeding after tooth extraction or bleeding after cavity preparation prior to filling. It can also be used effectively at the time of crown insertion by molding it over the freshly cemented crown where it will isolate the tooth from saliva and blood to prevent contamination of the unhardened cement, seal and hold the crown in occlusion, and pick up surplus cement. While natural fibers have been described as preferred for the absorbent medium, it will be understood that certain synthetic fibers with similar characteristics can also be used. The invention should not, therefore, be regarded as being limited except as defined in the following claims.

I claim:

1. In a method of gingival retraction and treatment, the steps of preparing a tooth for crowning by grinding the side walls into truncated conical configuration with the base disposed in the sub-gingival area not in excess of the depth of the sulcus to define a gingival trough between the ground-down walls of the tooth and the gingival flap of surrounding tissue, placing on the tooth a body of coherent flowable and moldable material having a substantial thickness at least approximating the length of the exposed portion of the tooth and having hydrosorbent characteristics at least at its surface, applying pressure on the body axially with respect to the tooth to cause the material to flow down the conical sides of the tooth and over the gingival tissue to envelop the gingival flap while absorbing liquid matter from within the trough and withdrawing the molded body axially from the tooth to establish a substantially dry gingival trough prepared for impression taking.

2. The method as set forth in claim 1 including the preliminary step of placing a small bead of coherent flowable material around the tooth and in the gingival trough, whereby the subsequent placement of the body of coherent flowable material having hydrosorbent characteristics applies gentle pressure to the bead while absorbing liquid matter displaced by the bead and attaching itself to the bead, whereby the bead and body become a single coherent mass to be withdrawn from the tooth, said flowable bead applying gentle outward pressure to the gingival flap to enlarge the trough before the hydrosorbent body balances the forces across the flap to fix the position thereof.

3. The method as set forth in claim 2 including the step of applying the vasoconstricting material to the flowable bead material.

4. The method as set forth in claim 1 in which the body of flowable coherent material is pressed over the prepared tooth and flowed both into the gingival trough and outside of the gingival flap to envelop the flap while filling the trough in the presence of balanced lateral forces across the flap to hold it substantially in its natural position.

5. The method as set forth in claim 1, including the step of applying a vasoconstricting material to the flowable material.

6. A dental device for gingival retraction and conditioning prior to taking an impression comprising a highly moldable body of flowable coherent thixatropic material having a substantial thickness at least approximating the length of the exposed portion of a tooth ground to form a gingival trough defined by a free standing flap of gingival tissue around the base of the tooth, said body having, substantial hydrosorbent characteristics at least at one of its surface, said mass being adapted to be pressed onto the prepared tooth, whereby pressure on the material causes it to flow over the tooth and over the gingival flap to absorb the liquid matter from the trough and to balance the lateral forces across the flap to hold it in position.

7. A dental device according to claim 6 in which the moldable body of coherent material is sufficiently flowable to enter and fill the gingival trough to absorb fluids therein.

8. A dental device as set forth in claim 6, in which the moldable body of coherent material has an affinity for related flowable material to unite therewith under light pressure, whereby a small bead of such material previously injected into the gingival trough will be placed under pressure by the body and will merge into a unitary structure therewith while the local liquids are absorbed and so that the unitary structure can be withdrawn from the tooth.

9. A dental device as set froth in claim 6, including an open thin walled rounded shell to contain the body and to distribute molding forces to the material.

10. A dental device as set forth in claim 6, a of the moldable body surface including a thin absorbent layer of fibers intimately bonded to at least that portion of the surface of the thixotropic mass which opposes the treatment site, whereby pressure-molding the mass onto the treatment site causes the moldable plastic to carry absorbent fibers throughout the surfaces and depressions of the treatment site.

11. A dental device as set forth in claim 10, said thixotropic mass having embedded therein a distribution of fibers beneath the absorbent layer to strengthen the surface fiber layer against tearing apart over distended portions of the molded material and exposing non-absorbent thixotropic material directly to the tissue of the treatment site.

12. A dental device as set forth in claim 11, said distribution of embedded fibers comprising one or more layers of concentrated fibers closely spaced to the surface layer.

13. A dental device as set forth in claim 11, said distribution of embedded fibers comprising between approximately two and four percent by weight of the thixotropic mass.

14. A dental device as set forth in claim 10, said absorbent surface layer of fibers being on the order of 0.03 to 0.2 mm. in thickness.

15. A dental device as set forth in claim 10, said surface layer of absorbent fibers comprising at least two discrete layers intimately bonded together.

16. A dental device as set forth in claim 15, said layers of surface fibers being bonded by an adhesive lightly dispersed between the surfaces to maintain porosity therebetween.

17. A dental device as set forth in claim 15, said layers of fibers being bonded by the thixotropic material extruded through interstices in the inner layer to mechanically entrain fibers in the outer layer.

18. A dental device as set forth in claim 17, said interstices being formed as apertures in the inner layer comprising in the aggregate less than ten percent of the surface area.

19. A dental device as set forth in claim 10, said layer of absorbent material being intimately bonded to the thixotropic material by the extrusion of minute fingers of thixotropic material into the interstices of the nonwoven layer.

20. A dental device as set forth in claim 10, including a relatively rigid housing containing the thixotropic mass and including at least one opening approximately the size of the treatment area to expose the absorbent fiber surface.

21. A dental device as set forth in claim 20, said housing being semi-cylindrical.

22. A dental device as set forth in claim 10, including a housing comprising lateral wall means surrounding the mass to expose at least one surface thereof, at least a portion of the lateral wall means being collapsible in response to tooth pressure normal to the exposed surface of the thixotropic mass.

23. A dental device as set forth in claim 22, at least a portion of the lateral wall means being absorbent.

24. A dental device as set forth in claim 22, said lateral wall means comprising a flexible material having substantial tensile strength, whereby the device can be molded laterally into a range of shapes to accommodate a range of tooth line contours.

25. A dental device as set forth in claim 22, said lateral means defining tooth receiving openings on both sides whereby the patient's tooth which opposes the tooth area under treatment operates as a piston to force the thixotropic mass onto the treatment site under the lateral constraint of the wall means.

26. A dental device as set forth in claim 25, including a relatively thick highly absorbent layer on the non-treatment side of the device.

27. A dental device as set forth in claim 10, including a vasoconstricting material entrained in said absorbent layer.

* * * * *

UNITED STATES PATENT OFFICE
CERTIFICATE OF CORRECTION

Patent No. 4,531,914            Dated July 30, 1985

Inventor(s) Ronald P. Spinello

It is certified that error appears in the above-identified patent and that said Letters Patent are hereby corrected as shown below:

Column 9, line 44, "head" should be --bead--.

Column 11, Claim 6, line 26 "thixatropic" should be --thixotropic--.

Column 11, Claim 10, line 54, after "claim 6, a" insert --surface--.

Column 11, Claim 10, line 55, cancel "surface".

Signed and Sealed this

Twenty-fourth Day of December 1985

[SEAL]

Attest:

DONALD J. QUIGG

Attesting Officer      Commissioner of Patents and Trademarks